United States Patent
Gau et al.

(10) Patent No.: US 6,518,836 B2
(45) Date of Patent: Feb. 11, 2003

(54) FREQUENCY-VARIATION TYPE DEMODULATOR AND DEMODULATING METHOD

(75) Inventors: Yow-Ling Gau, Taipei Hsien (TW); Chen-Nan Liao, Chungli (TW); Chen-Hua Hu, Taoyuan Hsien (TW)

(73) Assignee: Chung-Shan Institute of Science and Technology, Taoyuan (TW)

( * ) Notice: Subject to any disclaimer, the term of this patent is extended or adjusted under 35 U.S.C. 154(b) by 0 days.

(21) Appl. No.: 09/727,639

(22) Filed: Dec. 1, 2000

(65) Prior Publication Data

US 2002/0093376 A1 Jul. 18, 2002

(51) Int. Cl.[7] .................................................. H03D 3/00
(52) U.S. Cl. ........................ 329/341; 329/304; 375/324; 375/340
(58) Field of Search ................................ 329/341, 304; 375/324, 340; 327/105, 106, 107

(56) References Cited

U.S. PATENT DOCUMENTS 6,115,431 A * 9/2000 Lee ............................. 375/324

* cited by examiner

*Primary Examiner*—Arnold Kinkead
(74) *Attorney, Agent, or Firm*—J.C. Patents

(57) ABSTRACT

A frequency-variation type demodulator and demodulating method. A start signal is received by a control signal apparatus. After a delay time, a control signal is output. The control signal, a start frequency, a frequency variation slope and a clock are received by an in-phase and quadrature-phase function generator. A phase value is output via mathematical calculation. According to the phase value, a cosine and sine values are obtain by checking a phase look-up table in a first and a second ROM units, respectively. The cosine value is multiplied by a measured digital data in a first multiplier to obtain an in-phase demodulating signal, and the sine value is multiplied by the measured digital data to obtain a quadrature-phase demodulating signal.

10 Claims, 6 Drawing Sheets

FREQUENCY-VARIATION TYPE DEMODULATOR AND DEMODULATING METHOD

BACKGROUND OF THIS INVENTION

1. Field of the Invention

This invention relates to frequency-variation type demodulator and demodulating method, and more particularly, to a method to enhance operation speed and to reduce chip complexity applied to frequency-converting type demodulator and demodulating method.

2. Description of Related Prior Art

In the medical application, the ultrasonic inspection for a child conceived in a mother-to-be or for organs in human body has been widely applied. As the ultrasonic signal is propagating within the human organs, the central frequency of the ultrasonic is varied according to the transmitting depth within the organ. Thus, a required frequency is generated using a frequency-converting type demodulator.

FIG. 1A is a diagram showing the relationship between the frequency and time. FIG. 1B is a diagram showing another relationship between frequency and time. In FIG. 1A, $F_{start}$ represents a start frequency and $F_{slope}$ represents the slope of the frequency variation. The value of the frequency variation slope can be positive or negative. For example, in FIG. 1B, $F_{upslope}$ is a positive value, while $F_{downslope}$ is a negative value. In FIG. 1A, the magnitudes of $F_{start}$ and $F_{slope}$ are calculated from mathematical algorithm. The factors that affect $F_{start}$ and $F_{slope}$ include the attenuation coefficient of ultrasonic generated via traveling through different organs, and the transmitting depth within such organs. $F_{start}$ and $F_{slope}$ are used as input parameters provided for the demodulator. The detailed description is not illustrated here.

FIG. 2 shows a block diagram of a conventional demodulator. $f_P(t)$ represents a transient phase demodulating frequency, $f_D(t)$ represents a demodulating frequency profile, $t_P$ represents the demodulating reference time, and $t-T_{BREAK}$ is the time index after a turning frequency of the demodulating frequency. For example, in FIG. 1B, $F_{BREAK}$ is the break frequency of demodulating frequency, $t_R$ is the residue time, $f_{PC}(t)$ is the phase correction value, $f_{DV}(t)$ is the demodulating phase value, and $e^{j\Phi}$ is the phaser value.

When a demodulating frequency is applied from a data input to a phase and frequency processor 200, it is received via a frequency profile generator 202 in the phase and frequency processor 200. Meanwhile, the demodulating frequency is operated by mathematical algorithm to obtain the demodulating frequency profile $f_P(t)$ and the transient phase demodulating frequency $f_D(t)$.

A multiplication operation is performed on the demodulating frequency profile $f_P(t)$ and the demodulating reference time $t_D$ in the first multiplier 204. The result obtained from the multiplication is then added with a constant in the first adder 212. The result after the addition in the first adder 212 is the demodulating phase value $f_{DV}(t)$. In FIG. 1B, when the demodulating reference time $t_D$ is less than the break time $T_{BREAK}$, the demodulating reference time $t_D$ is output from a first multiplexer 208 to the first multiplier 204, while a constant of "0" is output from the second multiplexer 210 to the first adder 212. Meanwhile, the demodulating phase value is $f_{DV}(t)=f_D(t)\cdot t_D$. If the demodulating reference time $t_D$ is greater than the break time $T_{BREAK}$, the first multiplexer 208 outputs a demodulating reference time $t_D-T_{BREAK}$ to the first multiplier 204, and the second multiplexer 210 outputs a constant $f_D(T_{BREAK})\cdot T_{BREAK}$. Meanwhile, the demodulating phase is $f_{DV}(t)=f_D(t)\cdot(t_D-T_{BREAK})+f_D(T_{BREAK})\cdot T_{BREAK}$.

A multiplication operation is performed on the transient phase demodulating frequency $f_P(t)$ and the residue time $t_R$ in the second multiplier 206. The result for the multiplication operation is the phase correction value $f_{PC}(t)$. An addition operation is performed on the demodulating phase value $f_{DV}(t)$ and the phase correction value $f_{PC}(t)$ in the second adder 214. The added value is the phase value $\phi$.

Sine value and cosine value are built in a look-up table 216. When the phase value $\phi$ is input to the look-up table 216, a sine value and a cosine value corresponding to the input phase value $\phi$ are generated. A measured digital signal is input to a third multiplier 218 at DataIn, and a multiplication operation is performed with the sine of the phase value $\phi$, to obtain a quadrature-phase demodulating signal. The quadrature-phase demodulating signal is output to a subordinative circuit at OUTPUT. Similarly, a multiplication operation is performed on the measured digital signal and the cosine of the phase value $\phi$ to produce in an in-phase demodulating signal which is output to the subordinative circuit at OUTPUT.

The conventional demodulator requires a lot of multipliers for performing multiplication. When the digit number of the multiplier is large, the frequency is time varying and the multiplication has to be performed with a high speed operation clock, the operation of the demodulation cannot be achieved under the current technique. If the above method is to be implemented via hardware, there is a great difficulty in fabrication of integrated circuit.

SUMMARY OF THIS INVENTION

The invention provides frequency-variation type demodulator and demodulating method. A pipeline technique is used to reduce the computation load by addition or subtraction operation only. That is, adders or subtractors are used to replace the multipliers used in the conventional demodulator and demodulating method.

The demodulating method comprises the following steps. An initial value is received and delayed with a delay time to generate a control signal. The control signal, a start frequency, a frequency variation slope and a clock are provided to obtain a phase value via mathematical calculation. According to the phase value, a corresponding sine value and a corresponding cosine value are obtained from a look-up table. A digital signal is measured, then a multiplication operation is performed on the measured digital signal and the cosine value to obtain an in-phase demodulating signal. A multiplication operation is further performed on the measured digital signal and the sine value to obtain an out-of-phase demodulating phase.

In the demodulating method provided by the invention, the method for obtaining the phase value comprises the following steps. A parameter input value and a parameter address value are received. The parameter input value is allocated to obtain a start frequency and a frequency variation slope. A subtraction operation is performed on the start frequency and frequency variation slope to obtain the first differential.

A binary digit shift is performed on the frequency variation slope to obtain a shift value. An accumulated digit shift value, the digit shift value, the control signal and the clock are received to be performed with an addition operation, so that the updated accumulated digit shift value is obtained.

The first differential, the updated accumulated digit shift value, the control signal and the clock are received, and a subtraction operation is performed on the first differential and the updated accumulated digit shift value to obtain a second differential. The phase value obtain from the previous addition operation, the control signal, the second differential and the clock are received. An addition operation is performed on the phase value obtained from the previous addition operation and the second differential to obtain the phase value.

In the demodulator provided by the invention, a control signal apparatus comprises an input terminal and an output terminal. The input terminal receives the start signal, while the control signal is sent out from the output terminal after a delay time. An in-phase and quadrature-phase function generator comprises a first input terminal coupled to the output of the control signal apparatus to receive the control signal. The in-phase and quadrature-phase function generator further comprises a second input terminal to receive the start frequency, a third input terminal to receive the frequency variation slope and a fourth input terminal to receive the clock. Using mathematical calculation, a phase value can be derived at an output terminal.

The demodulator comprises a first and a second read only memory units and each of which includes an input terminal and an output terminal. The input terminals of the first and the second ROM units are coupled to the output terminal of the in-phase and quadrature-phase function generator to receive the phase value. According to the phase value, a corresponding cosine function value and a sine function value can be obtained from the cosine and sine function look-up tables in the first and the second ROM units. The output terminals of the first and second ROM units then output the cosine function value and the sine function value, respectively.

The first multiplier comprises a first input terminal to receive a measured digital data, a second input terminal coupled to the output terminal of the first ROM unit to receive the cosine value. A multiplication operation is performed on the measured digital data and the cosine value to obtain an in-phase demodulating signal which is output by the output terminal of the first multiplier. The second multiplier comprises a first input terminal to receive the measured digital data, a second input terminal coupled to the output of the second ROM unit to receive the sine value. The measured digital data is multiplied by the sine value within the second multiplier, so that a quadrature-phase demodulating signal is obtained at the output terminal of the second multiplier.

In another embodiment of the invention, a frequency-variation type digital demodulator is provided to comprise an in-phase and quadrature-phase function generator, a first and second subtractors, a shifter, and a first and second adders. The in-phase and quadrature-phase function generator comprises a parameter decoder. The parameter decoder comprises a first input terminal to receive a parameter input value and a second input terminal to receive a parameter address value. According to the parameter address value received at the second input terminal, the parameter input value is allocated. When the parameter input value is the start frequency, a first output terminal thereof outputs the start frequency. When the parameter input value is the frequency variation slope, the second output terminal thereof outputs the frequency variation slope.

The first subtractor comprises a first input terminal coupled to the first output terminal of the parameter decoder to receive the start frequency, and a second input terminal coupled to the second output terminal of the parameter decoder to receive the frequency variation slope. A subtraction operation is performed on the received start frequency and the frequency variation slope to obtain a first differential output by an output terminal of the first subtractor.

The shifter comprises an input terminal coupled to the second output terminal of the parameter decoder to receive the frequency variation slope. The frequency variation slope is shifted according to binary digit logic to obtain a phase shift value output by an output terminal of the shifter.

The first adder comprises four input terminals and an output terminal. The first input terminal is coupled to the output terminal of the first adder to receive a feedback of the accumulated added phase shift value obtained by a previous calculation. The second input terminal is coupled to the output terminal of the shifter to receive the phase shift value. The third input terminal is to receive the control signal, while the fourth input terminal is to receive the clock. The accumulation added phase shift value calculated by the previous addition operation is added with the phase shift value to obtain the accumulative added phase shift value which is then output to the output terminal.

The second subtractor comprises four input terminals and one output terminal. The first input terminal is coupled to the output terminal of the first subtractor to receive the first differential. The second input terminal is coupled to the output of the shifter to receive the accumulated phase shift value, the third input terminal is to receive the control signal, and the fourth input terminal is to receive the clock. The first differential and the accumulated phase shift value is subtracted with each other to obtain a second differential. The second differential is sent out to the output terminal.

The second adder comprises four input terminals and one output terminal. The first input terminal is coupled to the output of the second adder to receive the feedback of the phase value obtained by the previous addition operation. The second input terminal is coupled to the output terminal to receive the second differential. The third input terminal is to receive the control signal, and the fourth input terminal is to receive the clock. The phase value obtained from the previous addition operation and the second differential are added with each other to obtain a phase value output from the output terminal of the second adder.

Both the foregoing general description and the following detailed description are exemplary and explanatory only and are not restrictive of the invention, as claimed.

BRIEF DESCRIPTION OF DRAWINGS

The invention can be more fully understood by reading the following detailed description of the preferred embodiments, with reference made to the accompanying drawings.

PREFERRED EMBODIMENT

Figure 3:
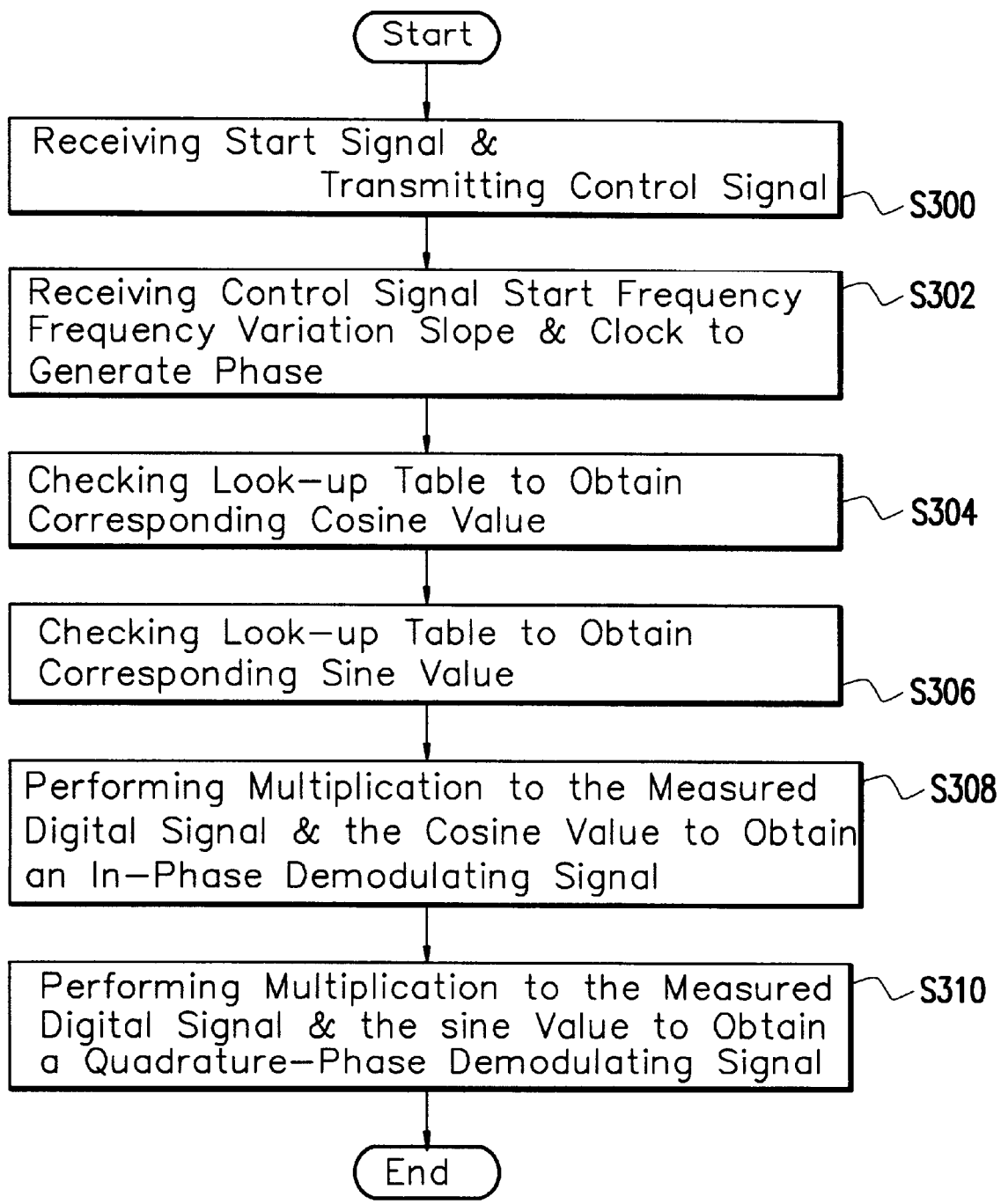
FIG. 3 is a flow chart for a method of frequency-type demodulation provided by the invention.
Figure 4:
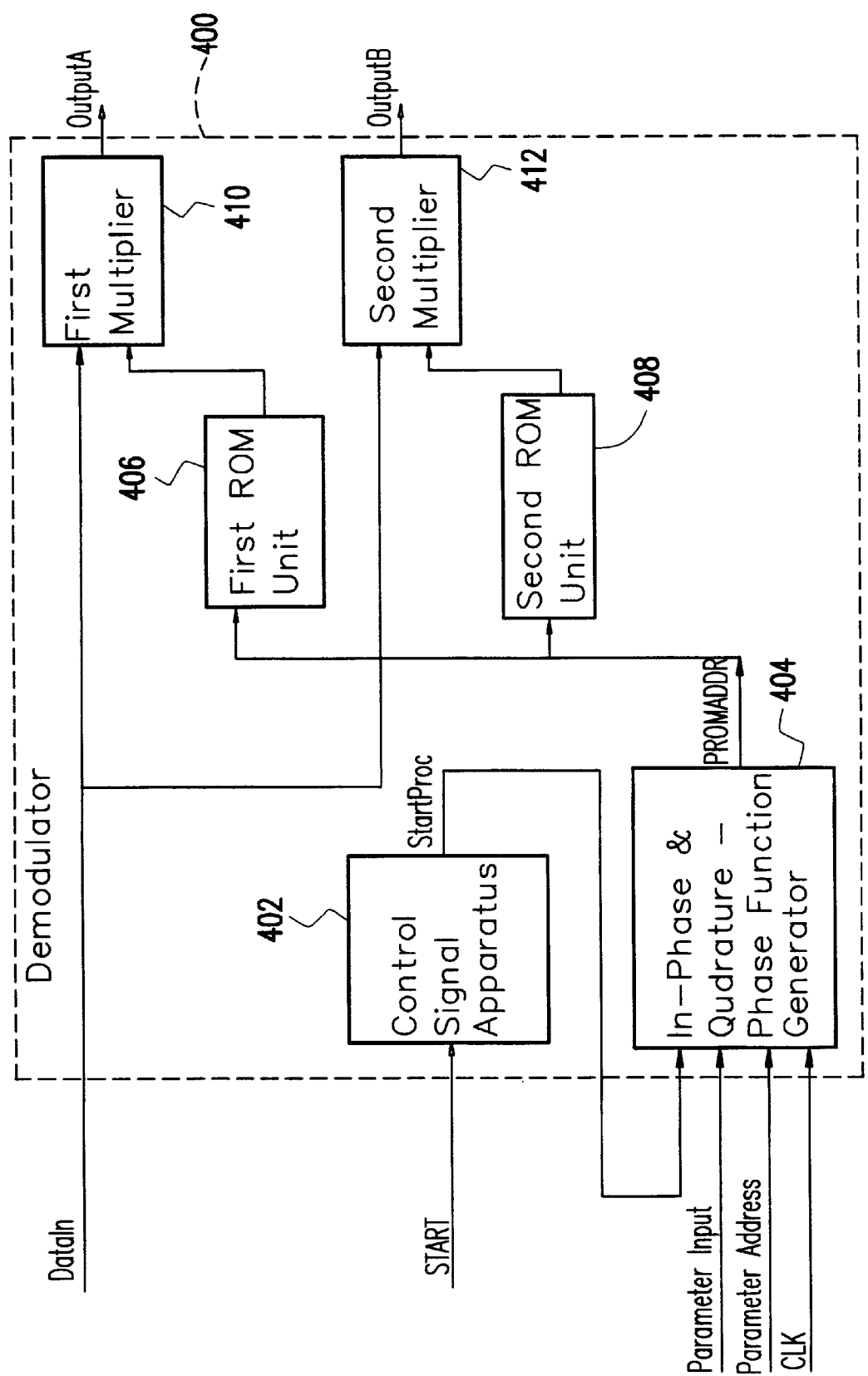
FIG. 4 is a block diagram showing a frequency-type demodulator provided by the invention.

FIG. 3 is a flow chart showing a frequency-variation type demodulating method in one embodiment of the invention. FIG. 4 shows a block diagram of a frequency-variation type demodulator provided by the invention. Referring to FIG. 3 and FIG. 4, when an ultrasonic instrument is performing an inspection, a demodulator 400 demodulates the input RF signal to baseband. In FIG. 4, a start signal is applied to a control signal apparatus 402 at START. After a delay time, a control signal is output at StartPRoc denoted as the step S300. The delay time is necessary for receiving and processing signal of the superordinary circuit of the demodulator 400. The delay time can be determined by external setup, for example, by a manual switch.

The control signal output at StartProc is applied to an in-phase and quadrature-phase function generator 404. Meanwhile, the control signal is in an enabling status to enable the in-phase and quadrature-phase function generator 404 to work. The required parameter and clock are input from the Parameter Input, Parameter Address ad CLK of the superordinary circuit of the demodulator. At the Parameter Input, an initial frequency and a frequency variation slope are applied. The in-phase and quadrature-phase function generator 404, generates a phase value by mathematical calculation in step S302. The phase value from the in-phase and quadrature-phase function generator 404 is then output at PROMADDR.

A cosine function look-up table is built in a first read-only memory (ROM) unit 406. By applying the phase value at PROMADDR into the first ROM 406, a corresponding cosine value is obtained by the cosine function look-up table as shown in step S304.

Similarly, a sine function look-up table is built up in a second read-only memory (ROM) unit 408. By applying the phase value to the second ROM unit 408, a corresponding sine value can be obtained by the sine function look-up table as described in step S306.

The cosine value is output from the first ROM unit 406 to a first multiplier 410. A measured digital data is input from DataIn of a circuit of the demodulator 400 to the first multiplier. The measured digital data is that data received and processes from the circuit of the demodulator. Meanwhile, a multiplication operation is performed on the in-phase signal and the measured digital data in the first multiplier 410 to obtain an in-phase demodulated signal in step S308. An in-phase demodulated signal is then output from the first multiplier 410 of a subordinary circuit of the demodulator 400.

Similarly, the sine value is output from the second ROM unit 408 to a second multiplier 412. A multiplication operation is performed on the sine value and the measured digit data to obtain a quadrature-phase demodulated signal in step S310. A quadrature-phase demodulated signal is then output from the second multiplier 412 to the subordinary circuit of the demodulator 400.

Figure 1A:
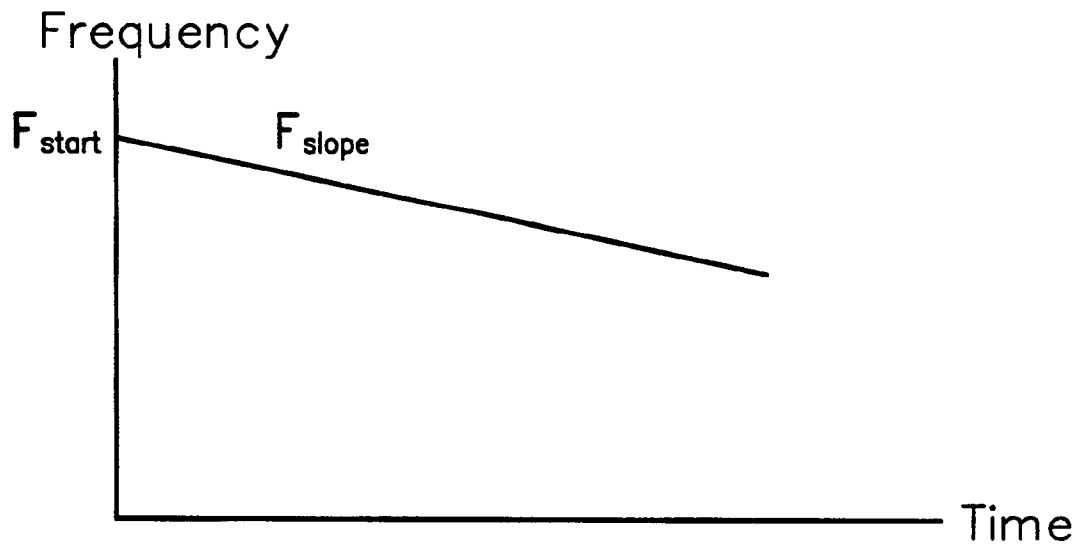
FIG. 1A is a diagram showing the relationship between frequency and time.
Figure 1B:
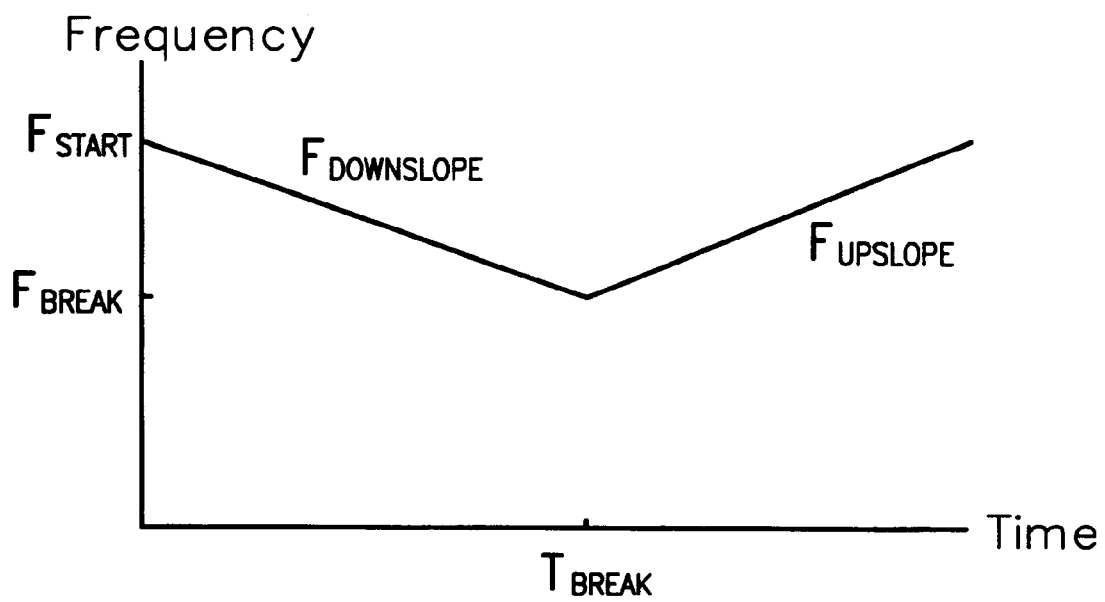
FIG. 1B is a diagram showing another relationship between frequency and time.
Figure 2:
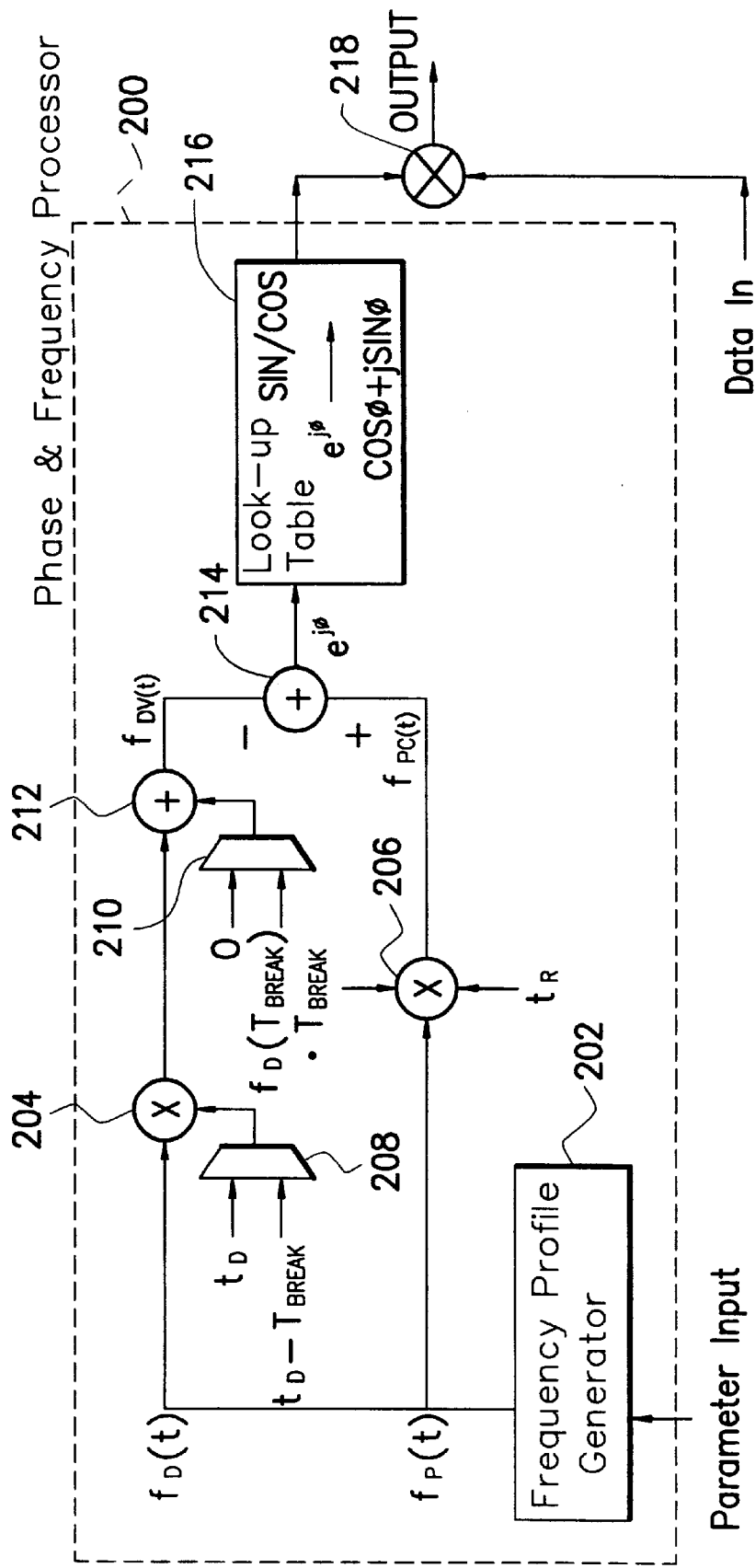
FIG. 2 is a block diagram showing a conventional demodulator.

As shown in FIG. 1A, the frequency is a linear time dependent function. The linear function is in the form of $f(t)=F_{start}-F_{slope} \cdot t$. Let $n \cdot t_0$ represent r, n to represent the sampling number, and $t_0$ represents the sampling time interval. The linear function can be rearranged as $f(n \cdot t_0)=F_{start}-F_{slope} \cdot n \cdot t_0$.

Since $t_0$ is a constant, it can be neglected during calculation as: $f(n) \cdot n = [F_{start}-F_{slope} \cdot n] \cdot n$. At the next sampling time, the linear function becomes:

$$F(n+1) \cdot (n+1) = [F_{start} - F_{slope} \cdot (n+1)] \cdot (n+1)$$

$$= n \cdot F_{start} + F_{start} - n^2 \cdot F_{slope} - 2 \cdot n \cdot F_{slope} - F_{slope}$$

$$= [F_{start} - F_{slope} \cdot n] \cdot n + F_{start} - 2 \cdot n \cdot F_{slope} - F_{slope}$$

$$= f(n) \cdot n + F_{start} - F_{slope} - 2 \cdot n \cdot F_{slope}$$

From the above calculation, it is clear that the operation of $f(n+1) \cdot f(n+1)$ can be obtained iteratively by adding a constant $(F_{start}-F_{slope})$ to the previous result $f(n) \cdot n$ and subtracting the last item $n \cdot (2 \cdot F_{slope})$. The last item $n \cdot (2 \cdot F_{slope})$ can be obtained by accumulation. Thus, the multiplication for $f(n) \cdot n$ can be simplified into accumulation or cumulative subtraction.

Regarding the external parameter, all the values of the parameters of decimals are taken as an example. For the parameter with the binary form, the most significant bit is multiplied by $2^{-1}$, and the next most significant bit is multiplied by $2^{-2}$. The remaining bits are operated with the same manner. The advantage of using the decimal is when the accumulation is larger than 1, the value can be represented by 1+x, where x represents the pure decimal. No matter for cosine function or sine function, the value for $2\pi(1+x)$ is equal to $2\pi x$. That is, the integer can be omitted.

Figure 5:
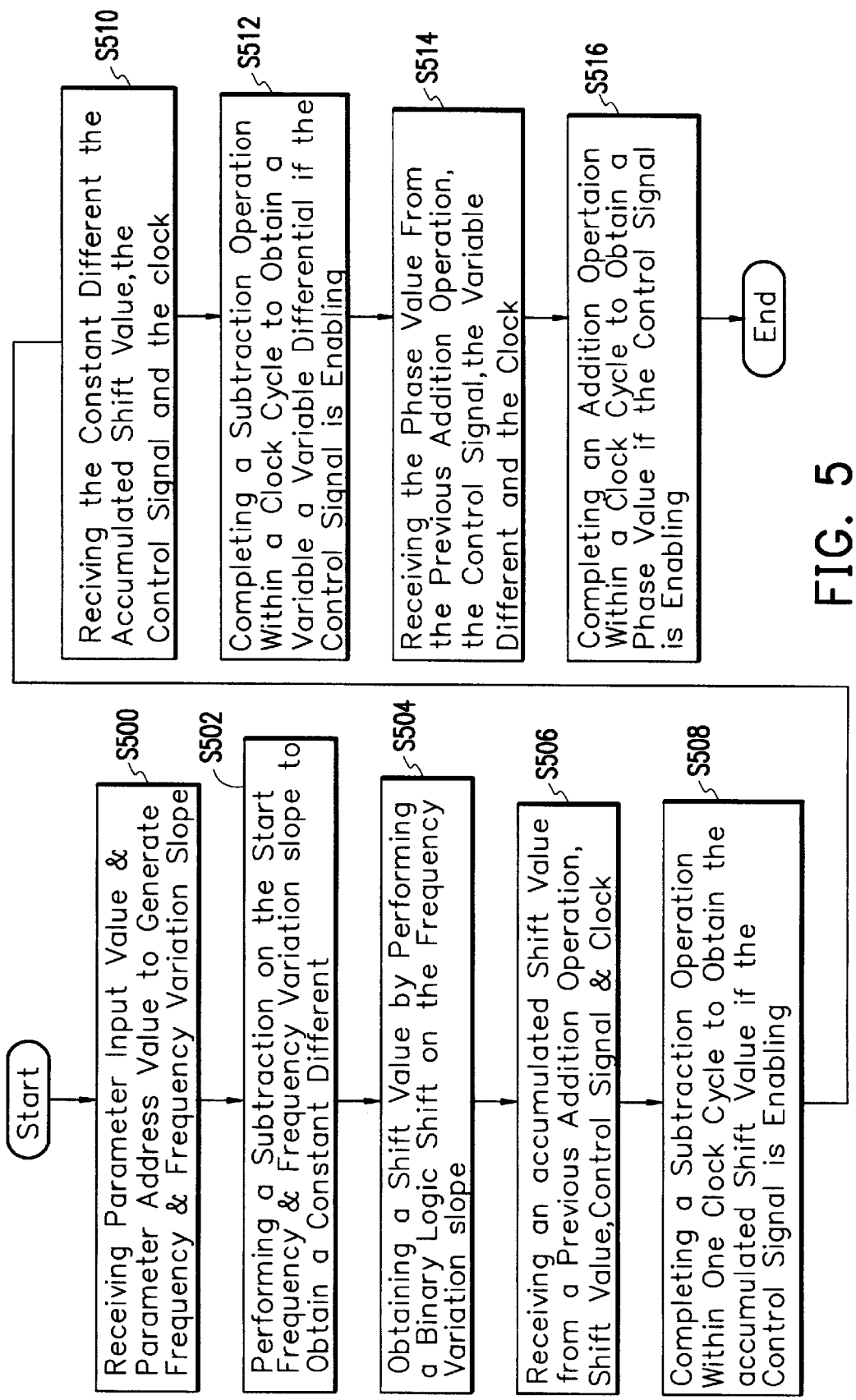
FIG. 5 is a flow chart of the method for generating the in-phase and quadrature-phase functions according to the invention.
Figure 6:
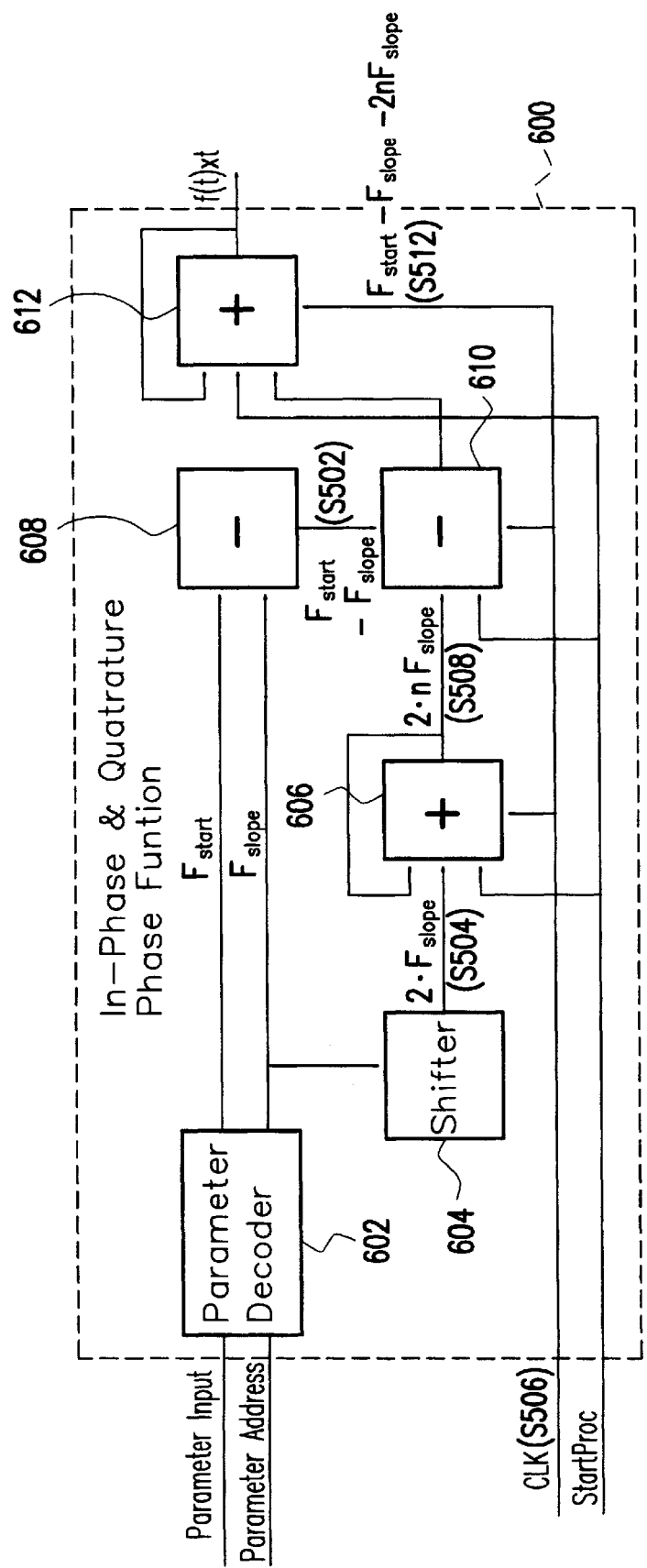
FIG. 6 shows the block diagram of an in-phase and quadrature-phase function generator according to the invention.

FIG. 5 shows a flow chart for the generation method of the in-phase and quadrature-phase function. FIG. 6 shows a block diagram of the in-phase and quadrature-phase generator. The start frequency $F_{start}$ and the frequency variation slope $F_{slope}$ are input at Parameter Input from the external circuit to the parameter decoder of the in-phase and quadrature-phase function generator 600. Meanwhile, the parameter address is applied at Parameter Address from the external circuit to the parameter decoder 602 of the in-phase and quadrature-phase function generator 600. According to the parameter address received at Parameter Address, the parameter decoder 602 can recognize whether the received data is the start frequency $F_{start}$ or the frequency variation slope $F_{slope}$(S500).

For example, if the parameter decoder 602 receives a parameter address 0 at the Parameter Address, the start frequency $F_{start}$ is received at the Parameter Input, and the start frequency $F_{start}$ appears at the first terminal of the parameter decoder 602. If the parameter address is 1, the frequency variation slope $F_{slope}$ is received at the Parameter Input, and the parameter decoder 602 outputs the frequency variation slope $F_{slope}$ at the second output terminal.

The start frequency $F_{start}$ out of the parameter decoder 602 is applied to the input of a first input terminal of a first subtractor 608, while the frequency variation slope $F_{slope}$ out of the parameter decoder 602 is applied to a second input terminal of the first subtractor 608. The start frequency $F_{start}$ and the frequency variation slope $F_{slope}$ are subtracted by each other to obtain a constant difference $F_{start}-F_{slope}$ (S502). The constant difference $F_{start}-F_{slope}$ is then fed to a second subtractor 610.

The frequency variation slope $F_{slope}$ is further applied to the input of the shifter 604 from the parameter decoder 602. The frequency variation slope $F_{slope}$ is further operated with a binary logic shift to obtain a shifted value $2 \cdot F_{slope}$(S504). The shift value $2 \cdot F_{slope}$ out of the output terminal of the shifter 604 applied to the first adder 606.

The first adder comprises four input terminals. The first terminal is coupled to the output terminal of the first adder 606, so that the accumulated phase shifted value n·(2·$F_{slope}$) at the output terminal can be fed back to the first input terminal. A second input terminal is coupled to the output terminal of the shifter 604. The shift value 2·$F_{slope}$ out of the shifter 604 is applied to the second terminal of the first adder 606. A third input terminal of the first adder 606 is coupled to StartProc to receive the control signal provided by the external circuit. A fourth input terminal of the first adder 606 is to receive the clock provided by the external circuit at CLK (S506).

When the control signal received by the third input terminal of the first adder 606 is enabled, the first adder 606 starts operation. The first adder 606 performs one addition operation during a clock cycle. Thus, after one clock cycle, the output feedback accumulated shift value n·(2·$F_{slope}$) is added with the shifted value 2·$F_{slope}$ received by the second input terminal. A new accumulation shift value n·(2·$F_{slope}$) is obtained by the addition operation (S508). The new accumulated shift value at the output terminal of the first adder 606 n·(2·$F_{slope}$) applied to the input of the second subtractor 610.

The second subtractor 610 comprises four input terminals. The first input terminal is coupled to an output terminal of the first subtractor 608, so that the constant differential $F_{start}-F_{slope}$ is applied to the first input terminal of the second subtractor 610. The second input terminal is coupled to the output terminal of the first adder 606 to receive the accumulated shift value n·(2·$F_{slope}$) The third input terminal is to receive the control signal at StartProc provided by the external circuit. The fourth input terminal is to receive the clock at CLK provided by the external circuit (S506).

When the control signal received by the third input terminal of the second subtractor 610 is enabled, the second subtractor starts operation. The fourth input terminal receives the clock to complete one subtraction operation within the clock. Thus, at a clock period, the constant differential $F_{start}-F_{slope}$ received by the first terminal and the accumulated shift value n·(2·$F_{slope}$) are subtracted by each other to obtain a variable differential $F_{start}-F_{slope}-$n·(2·$F_{slope}$) (S512). The output terminal of the second subtractor outputs the variable differential $F_{start}-F_{slope}-$n·(2·$F_{slope}$) to the second adder 612.

The second adder 612 comprises four input terminals, a first input terminal is coupled to the output terminal itself The output terminal outputs a phase value $f(t)·t$ which is fed back to the first input terminal. The second input terminal of the second adder 612 is coupled to the output terminal of the second subtractor 610, to receive the variable differential $F_{start}-F_{slope}-$n·(2·$F_{slope}$). A third input terminal is to receive the control signal at StartProc provided by the external circuit, and a fourth input terminal is to receive the clock at CLK provided by the external circuit.

When the control signal received by the third input terminal is enabled, the second adder 612 starts to operation. One addition operation is completed within one clock cycle with the clock received by the fourth input terminal. Thus, within one clock cycle, the second adder 612 performs one addition operation on the feedback phase shift value $f(t)·t$ and the variable differential $F_{start}-F_{slope}-$n·(2·$F_{slope}$). The resultant is a new phase value $f(t)·t$ (S516). From the output terminal of the second adder 612, the new accumulated phase shift value n·(2·$F_{slope}$) is applied to a subordinary circuit.

Thus, this invention includes the advantage of simplifying the multiplication operation by addition/subtraction, that is, adders and subtractors replace the multiplier, while the same function can still be achieved.

This invention further includes the advantage of generating time dependent frequency variation, such that the frequency function obtained by multiplier is converted into the frequency function obtained by the adder and subtractor, hense the complexity of hardware design is reduced.

Furthermore, this invention includes the advantage of representing the frequency related parameters by decimals, so that the digit number of the adder and the subtractor is reduced, while the same precision is still hold.

Other embodiments of the invention will appear to those skilled in the art from consideration of the specification and practice of the invention disclosed herein. It is intended that the specification and examples to be considered as exemplary only, with a true scope and spirit of the invention being indicated by the following claims.

What is claimed is:

1. A frequency-variation type demodulating method, comprising:

receiving a start signal;

generating a control signal by delaying the start signal;

receiving the control signal, a start frequency, a frequency variation slope and a clock to enable an in-phase and qudrature-phase function generator to generate a phase value;

receiving the phase value to obtain a corresponding cosine function value by checking a phase look-up table;

obtaining a corresponding sine function value by checking the phase look-up table;

receiving a measured digital signal, and performing a multiplication operation on the measured digital signal and the cosine function value to obtain an in-phase demodulating signal; and performing a multiplication operation on the measured digital signal and the sine function value to obtain a quadrature-phase demodulating signal.

2. The method according to claim 1, wherein the step of generating the phase value comprises:

receiving a parameter input value and a parameter address value, and allocating the parameter input value after receiving the parameter address value, so as to generate the start frequency and the frequency variation slope;

receiving the start frequency and the frequency variation slope and performing a subtraction operation to obtain a first differential;

generating a phase shift value by shifting digits of the frequency variation slope;

receiving an accumulated phase shift value obtained by a previous addition operation, the phase shift value, the control signal and the clock to perform an addition operation on the accumulated phase shifted value and the phase shift value to obtain an updated accumulated phase shift value;

performing a subtraction operation on the first differential and the updated accumulated phase shift value to obtain a second differential; and performing an addition operation on the accumulated phase shift value by the previous addition operation and the second differential to obtain the phase value.

3. The method according to claim 2, wherein the step of performing an addition operation on the accumulated phase shift value and the phase shift value is performed within a clock cycle when the control signal is enabling.

4. The method according to claim 2, wherein the step of performing a subtraction operation on the first differential and the updated accumulated phase shift value is performed within a clock cycle when the control signal is enabling.

5. The method according to claim 2, wherein the step of performing an addition operation on the accumulated phase shift value by the previous operation and the second differential is performing within a clock cycle when the control signal is enabling.

6. A frequency-variation type digital demodulator, comprising:
a control signal apparatus, comprising an input terminal and an output terminal, the input terminal is to receive a start signal which is delayed with a delay time to output a control signal at the output terminal;
an in-phase and quadrature-phase function generator, comprising a first, a second, a third and a fourth input terminals and an output terminal, wherein the first input terminal is coupled to the output terminal of the control signal apparatus to receive the output signal, the second input terminal is to receive a start frequency, the third terminal is to receive a frequency variation slope, the fourth terminal is to receive a clock, and a phase value is obtained output by the output terminal;
a first read only memory unit, comprising an input terminal and an output terminal, the input terminal being coupled to the output terminal of the in-phase and quadrature-phase function generator to receive the phase value, so that a corresponding cosine value is obtained by checking a phase look-up table and output by the output terminal;
a second read only memory unit, comprising an input terminal and an output terminal, the input terminal being coupled to the output terminal of the in-phase and quadrature-phase function generator to receive the phase value, so that a corresponding sine value is obtained by checking a phase look-up table and output by the output terminal;
a first multiplier, comprising a first and a second input terminals and an output terminal, wherein the first input terminal is to receive a measured digital data, the second input terminal is coupled to the output terminal of the first read only memory unit to receive the cosine value, the first multiplier performs a multiplication on the measured digital data and the cosine value to obtain an in-phase demodulating signal output from the output terminal; and
a second multiplier, comprising a first and a second input terminals and an output terminal, wherein the first input terminal is to receive a measured digital data, the second input terminal is coupled to the output terminal of the second read only memory unit to receive the sine value, the second multiplier performs a multiplication on the measured digital data and the sine value to obtain a quadrature-phase demodulating signal output from the output terminal.

7. A variation type demodulator, comprising an in-phase and quadrature-phase function generator which further comprises:
a parameter decoder, comprising further:
a first input terminal, to receive a parameter input value;
a second input terminal, to receive a parameter address value which is allocated after receiving the parameter input value;
a first output terminal, to output a start frequency when the parameter input value is the start frequency; and
a second output terminal, to output a frequency variation slope when the parameter input value is the frequency variation slope;

a first subtractor, comprising:
a first input terminal, coupled to the first output terminal of the parameter decoder to receive the start frequency;
a second input terminal, coupled to the second output terminal of the parameter decoder to receive the frequency variation slope; and
an output terminal, to output a first differential obtained by performing a subtraction operation on the start frequency and the frequency variation slope;
a shifter, comprising:
an input terminal, coupled to the second output terminal to receive the frequency variation slope; and
an output terminal, to output a phase shift value obtained by shifting digits of the frequency variation slope;
a first adder, comprising:
a first input terminal, coupled to an output terminal of the first adder to receive a feedback of an accumulated phase shift value of a previous addition operation;
a second input terminal, coupled to the output terminal shifter to receive the phase shift value;
a third input terminal, to receive a control signal to enable the first adder;
a fourth input terminal, to receive a clock; and
the output terminal, to output an updated accumulated phase shift value obtained by adding the accumulated phase shift and the phase shift;
a second subtractor, comprising:
a first input terminal, coupled to the output terminal of the first subtractor to receive that first differential;
a second input terminal, coupled to the output terminal of the first adder to receive the updated accumulated phase shift value;
a third input terminal, to receive the control signal to enable the second subtractor;
a fourth input terminal, to receive the clock; and
an output terminal, to output a second differential obtained by performing a subtraction operation on the first differential and the updated accumulated phase shift value; and
a second adder, comprising:
a first input terminal, coupled to an output terminal output terminal to receive a feed back of a phase value obtained by a previous addition operation;
a second input terminal, coupled to the output terminal of the second subtractor to receive the second differential;
a third input terminal, to receive the control signal;
a fourth input terminal, to receive the clock; and
the output terminal, to output an updated phase value obtained by performing an addition operation on the phase value and the second differential.

8. The demodulator according to claim 7, wherein the addition operation performed in the first adder is performed within a clock cycle when the control signal is enabling.

9. The demodulator according to claim 7, wherein the subtraction operation performed in the second subtractor is performed within a clock cycle when the control signal is enabling.

10. The method according to claim 1, wherein the addition operation performing in the second adder is performed within a clock cycle when the control signal is enabling.

* * * * *